United States Patent [19]
Baudino

[11] Patent Number: 5,954,687
[45] Date of Patent: Sep. 21, 1999

[54] BURR HOLE RING WITH CATHETER FOR USE AS AN INJECTION PORT

[75] Inventor: Michael D. Baudino, Coon Rapids, Minn.

[73] Assignee: Medtronic, Inc., Minneapolis, Minn.

[21] Appl. No.: 08/430,781

[22] Filed: Apr. 28, 1995

[51] Int. Cl.$^6$ .................................................. A61M 31/00
[52] U.S. Cl. ........................... 604/48; 604/93; 604/174; 604/175
[58] Field of Search ............................ 604/93, 167, 174, 604/175, 48, 51, 264, 272, 274

[56] References Cited

U.S. PATENT DOCUMENTS

| | | | |
|---|---|---|---|
| 4,821,716 | 4/1989 | Ghajar et al. ....................... | 604/174 X |
| 4,840,617 | 6/1989 | Osterholm ............................ | 604/174 |
| 4,931,056 | 6/1990 | Ghajar et al. ....................... | 604/174 X |
| 5,045,060 | 9/1991 | Melsky et al. ....................... | 604/175 X |
| 5,092,849 | 3/1992 | Sampson .............................. | 604/175 |
| 5,122,114 | 6/1992 | Miller et al. ....................... | 604/175 X |
| 5,372,583 | 12/1994 | Roberts et al. ..................... | 604/51 |

*Primary Examiner*—Sam Rimell
*Assistant Examiner*—Robert V. Racunas
*Attorney, Agent, or Firm*—Curtis D. Kinghorn; Harold R. Patton

[57] ABSTRACT

A burr hole ring with a catheter for use as an injection port comprises a modified burr hole ring adapted to engage the skull at a burr hole drilled therein. The interior of the burr hole ring defines a fluid reservoir that may be accessed by a needle or stylet inserted through a septum positioned over the top of the burr hole ring. The reservoir is in fluid communication with the central lumen of a catheter. The assembly comprises a fluid flow path suitable for the transfer of fluids to or from selected location at, near or within the brain. A filter layer may be provided to prevent contamination of the drug infusion site.

29 Claims, 4 Drawing Sheets

BURR HOLE RING WITH CATHETER FOR USE AS AN INJECTION PORT

BACKGROUND

The present invention relates generally to methods and apparatus for providing a low profile access port establishing fluid communication with the brain, such as for the administration of drugs or other liquids to specific locations within the body; and further relates to brain infusion procedures, such as, for example, supplying pharmaceutical agents such as peptides, polypeptides, proteins, glycoproteins, lipoproteins, oligonucleotides, oligonucleosides, hormonal agents, and/or other biologically derived trophic agents to the lateral ventricle of the brain. Although this particular application is the one described in detail herein, it should be understood that the invention is not necessarily so limited.

Physicians today often use a catheter placed to extend to a selected location within a patient's brain for both the administration of fluids and the receiving of fluids. Using conventional apparatus to deliver pharmaceutical agents to a catheter for delivery to a specific location within the brain, however, has significant drawbacks. For example, the catheter will typically extend outwardly from the burr hole. Where only periodic administration of fluids are necessary, the extending catheter presents an unnecessary encumbrance. It would be desirable to remove this encumbrance.

Accordingly, the present invention provides a new method and apparatus for establishing fluid communication through a catheter to a selected point within a patient's brain, which maybe selectively accessed to inject fluid into, or withdraw fluid from, the brain through the catheter.

SUMMARY OF THE INVENTION

As explained in more detail below, the present invention overcomes the above-noted and other shortcomings of prior devices and methods for facilitating the infusion of drugs to the brain. Three separate exemplary embodiments of the present invention are described herein.

The first exemplary embodiment generally comprises a burr hole ring modified to act as a catheter access port. The device may be integrally attached to a catheter of a length sufficient for delivering drugs to a desired location within the skull, or may be attached following catheter placement. Preferably, in accordance with the present invention, a catheter integrally attached to a modified burr hole ring assembly is inserted to a desired depth and placement within the brain, typically being placed with the use of a stylet (a thin, solid wire or similar relatively non-flexible member) inserted through the catheter access port and into the catheter to maintain its rigidity. Once the catheter is placed, the stylet is withdrawn and the modified burr ring or cap assembly is secured within the burr hole in the skull. Securing the cap assembly may be accomplished with screws inserted through the assembly and into the skull. More preferably, though, the modified burr ring assembly is adapted with threads or ridges for engaging the skull at the burr hole. A septum positioned on top of the burr ring or cap assembly isolates the interior of the catheter access port to help prevent contamination of fluids within the assembly. A needle fixed to an appropriate device may be used to penetrate the septum as desired to either withdraw or inject fluid. In accordance with the present invention, filtration of injected fluids also may be accomplished. Preferably, filtration is achieved by a filter member that is bacterial retentive so as to prevent contamination of the cerebral spinal fluid. The cap assembly may be adapted so that there is a filtering layer above the central tube which permits direct fluid communication between the interior of the catheter and the interior of the cap assembly. Above the filtering layer is positioned a needle stop, so that the injection or withdrawal of fluid is accomplished by the needle penetrating the septum until it hits the needle stop material. Any injected fluid then passes through the filter, central tube and catheter to the desired location within the patient's body.

As compared to the first exemplary embodiment described above, in a second exemplary embodiment the catheter access port assembly further comprises a direct-feed, generally tubular member extending through the septum and into the central tube. The direct-feed tubular member allows direct, unfiltered, fluid access from a location at the top of the septum through the central tube an into the interior of the catheter. Fluid within the interior of the catheter access port assembly may still flow along a path through the filter medium to the annular space between the central tube and the direct-feed tubular member. The second exemplary embodiment thus affords the physician more than one fluid path option for the injection or withdrawal of fluids.

In a third exemplary embodiment, a burr hole cap having an integrally coupled catheter is placed in engagement with the skull at a burr hole. A septum mounting member, comprising a generally rigid collar-like member, preferably snaps through use of split-flanged collets into the burr hole cap, although other means for securing the septum mounting member to the burr hole cap may be used, e.g. edge fasteners, clamps, adhesives, etc. The septum secured in the top portion of the septum mounting member again facilitates isolation of, yet selective access through a needle to, the filtered fluid path through which fluids may be injected or withdrawn. The septum mounting member preferably also is adapted with circumferential snap fittings and a perforated base to facilitate insertion into the member of one or more selected pieces of filter medium. The filtering material is placed on the perforated base of the member, and a perforated filter cap is then snapped into the member to hold the filter in place. The perforated filter cap also may act as a needle stop. Preferably, the filter assembly also is detachable, thus having the advantage that the filter medium could be removed or the filter assembly replaced to resurrect a non-fuinctioning port (e.g., a port having a dirty or clogged filter that overly restricts fluid flow).

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

DETAILED DESCRIPTION OF THE INVENTION

Figure 1:
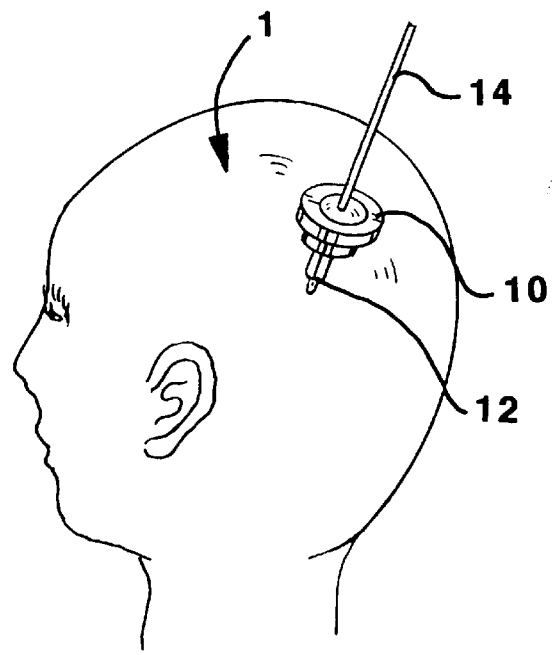
FIG. 1 is an illustration of an exemplary burr hole cap assembly in accordance with the present invention.

As illustrated in FIG. 1, the present invention is a fluid communication port generally labeled 10. In particular, the invention has particular application with an attached catheter 12 for use to establish fluid communication with a location inside a patient's brain 1. The fluid communication port 10 may be used as an injection port in connection with the infusion of drugs to specific locations within the brain 5. Placement of the fluid communication port 10 is facilitated through the use of a stylet 14 placed through the fluid communication port 10 and within the catheter 12 to enhance its rigidity during insertion into the brain 1. One advantage of the present invention is that following the withdrawal of stylet 14, the positioned fluid communication port 10 has a low, relatively unobtrusive profile.

Figure 2:
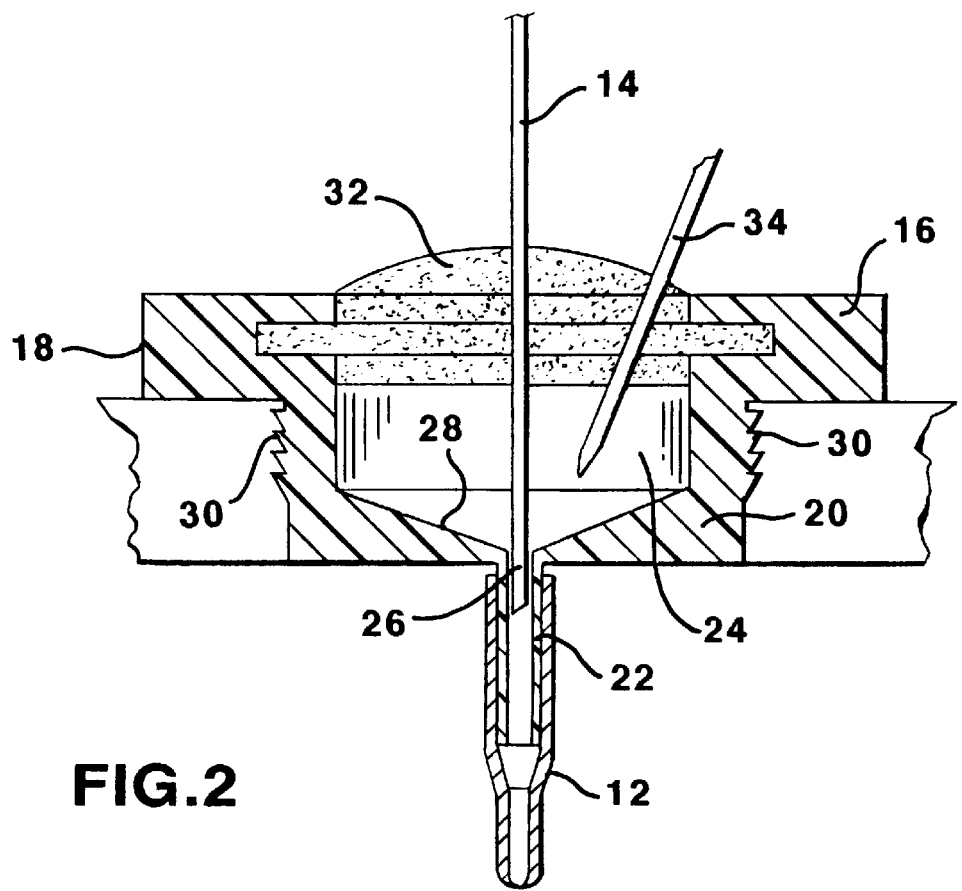
FIG. 2 is an illustration of an exemplary modified burr ring assembly in mechanical engagement with a catheter in accordance with the present invention, depicted in a vertical cross-sectional view.

The first embodiment of the present invention is depicted in FIG. 2. This embodiment comprises a burr hole ring 16 having an upper flange portion 18, a lower burr hole engaging portion 20, and a central connection tube 22 which permits fluid communication between a catheter 12 and a fluid reservoir 24 within the burr hole ring 16. Central connection tube 22 is connected to burr hole ring 16 and has an upper opening 26 that is in fluid communication with fluid reservoir 24. Catheter 12 is attached to central connection tube 22. This may be done by conventional telescoping or bayonet engagement. Preferably, the inner surface 28 of the lower portion 20 is tapered, facilitating the flow of any liquid within fluid reservoir 24 into the central connection tube 22.

The outer surface of lower portion 20 preferably is adapted with a mechanism for mechanically engaging a burr hole drilled through the skull. As shown in FIG. 2, the burr hole engaging means preferably comprises threads or ridges 30 adapted to engage the inner sides of the burr hole. However, screws or other suitable anchoring means may be used to secure the burr hole ring 16 to a patient's skull.

The central connection tube 22 extends within the catheter 12 as a means of facilitating fluid delivery to within the catheter. The central connection tube 22 also may act as a guide to ease the entry of a stylet 14 into the central lumen of catheter 12.

A septum 32 placed in the top portion of the modified burr hole ring 16 isolates the fluid reservoir 24 from the ambient environment. Providing a desired pharmaceutical agent to the fluid reservoir 24 for delivery to a specific location within the body may be accomplished by inserting a hypodermic needle 34 or other similar device through the septum 32 to inject the fluid agent. The septum 32 will preferably be formed of a silicone elastomer selected to be self-sealing to punctures by a needle or stylet of the size anticipated to be utilized for fluid delivery to fluid reservoir 24.

In use, catheter 12 is cut to a predetermined length and attached to central connection tube 22. A stylet 14 is inserted through septum 32 into central connection tube 22 and ultimately into catheter 12. Stylet 14 adds rigidity to catheter 12. Catheter 12 is then inserted into the patient's brain 1 and moved to a desired location whereupon, burr hole ring 16 moves into the burr hole formed in the patient's skull. The addition of stylet 14 facilitates placement of the catheter 12 within the patient's brain 1.

Figure 3:
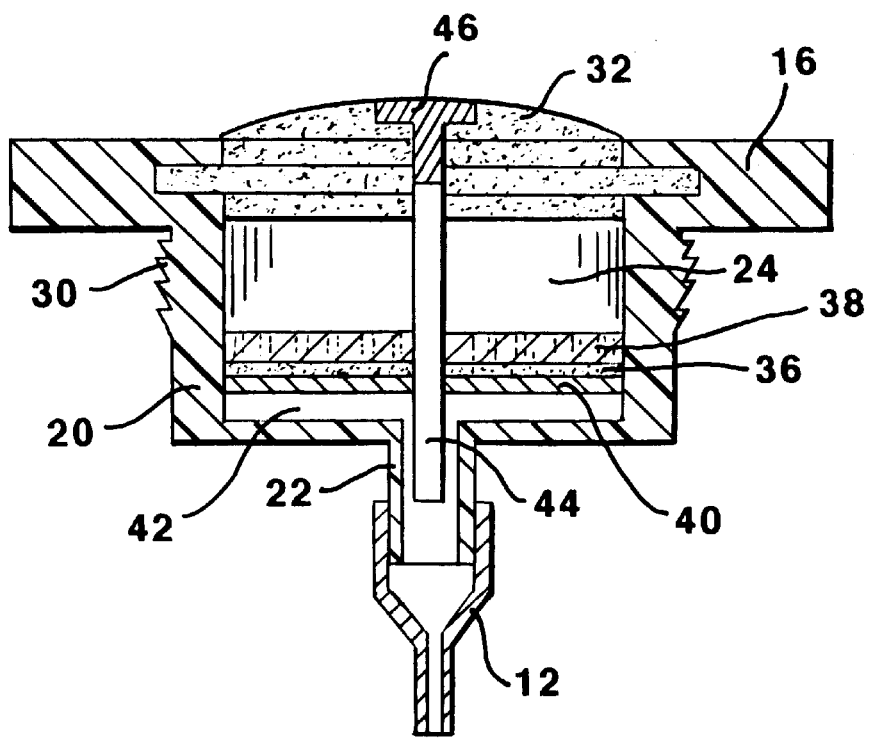
FIG. 3 is an illustration of an exemplary burr hole cap assembly in accordance with the present invention with an exemplary direct-feed tubular member defining an exemplary additional fluid flow path, depicted in a vertical cross-sectional view.

An alternate embodiment of the present invention is shown in FIG. 3. This embodiment, similar to the previous embodiment, has a burr hole ring 16, an upper flange portion 18, a lower burr hole engaging portion 20 and a central tube 22. In this embodiment, a filtering means is added to filter the infusate. The filtering means comprises a filtering layer 36, a needle stop 38 and perforated base 40 which forms a filter assembly. Filtering layer 36 is positioned within burr hole ring 16. In this embodiment, a lower fluid reservoir 42 is formed below filtering layer 36. Central tube 22 is in fluid communication with lower fluid reservoir 42. In this way, fluids from upper reservoir 24 are filtered prior to entering central tube 22.

Filtering layer 36 filters bacteria and other particulate matter from the liquid being infused into the patient. Preferably, filtering layer 36 comprises a bioretentive material. An exemplary material would be a polyvinylidene fluoride membrane having a maximum pore size of 0.22 microns. Such a filter should retain its filtering characteristics after subjection to a sterilization process.

A needle stop 38 is positioned above filtering layer 36 and perforated base 40 is positioned below filtering layer 36. The combination of needle stop 38 above and perforated base 40 below holds filtering layer 36 in place and forms a seal around filtering layer 36 so that all fluid entering catheter 12 must pass through filtering layer 36. Needle stop 38 is preferably a highly porous, preferably perforated, generally rigid member. This prevents passage of a needle through filtering layer 36, but allows passage of the infusate to filtering layer 36. Perforated base 40 should also be porous to allow fluid to pass into lower reservoir 42. In addition, perforated base 40 should be rigid enough to act as a support for filtering layer 36. This configuration of needle stop 38 and perforated base 40 assures that any injected fluid will pass through the filter material of filtering layer 36 prior to entering central tube 22.

Septum 32 covers fluid reservoir 24 and isolates fluid reservoir 24 from the external environment to prevent contamination of the fluid within fluid reservoir 24. A stylet tube 44 extends through septum 32 into central connection tube 22. The stylet tube 44 acts as a guide for an inserted stylet 14, ensuring accurate placement of stylet 14 within the catheter 12.

Stylet tube 44 is in sealing communication with both septum 32 and needle stop 38 and filtering layer 36. This ensures fluid from fluid reservoir 24 must pass through filtering layer 36 before entering lower reservoir 42. However, it is essential that fluid in lower reservoir 42 be able to enter central connection tube 22. This may be accomplished by making stylet tube 44 narrower that the inner diameter of central connection tube 22 so that fluid may enter central connection tube 22 by flowing around stylet tube 44. This may also be accomplished by perforating stylet tube 44 only within lower reservoir 42 so that fluid in lower reservoir 42 may enter stylet tube 44 through the perforations. Fluid entering stylet tube 44 through the perforations flows into central connection tube 22 by flowing through and out of the end of stylet tube 44.

In use, as above, catheter 12 is cut to a predetermined length and attached to central connection tube 22. A stylet 14 is inserted through stylet tube 44 into central connection tube 22 and ultimately into catheter 12. The addition of filtering layer 36 ensures that the fluid delivered to the patient's brain 1 is filtered. Stylet tube 44 allows a stylet 14 to be used with the filtering layer 36 so that the advantages of both having a filter and a stylet are realized in a single device. Catheter 12 is then placed in the patient's brain 1 as described above.

Upon withdrawal of the stylet 14, a sealing plug 46 or other suitable device is inserted into the stylet tube 44 to prevent any unfiltered flow from entering catheter 12. Preferably, sealing plug 46 is made of a biocompatible material such as titanium or other biocompatible metal or a hard biocompatible polymer such as polysufone. Regardless of the material chosen for sealing plug 46, sealing plug 46 should be impenetratable by a needle.

Figure 4:
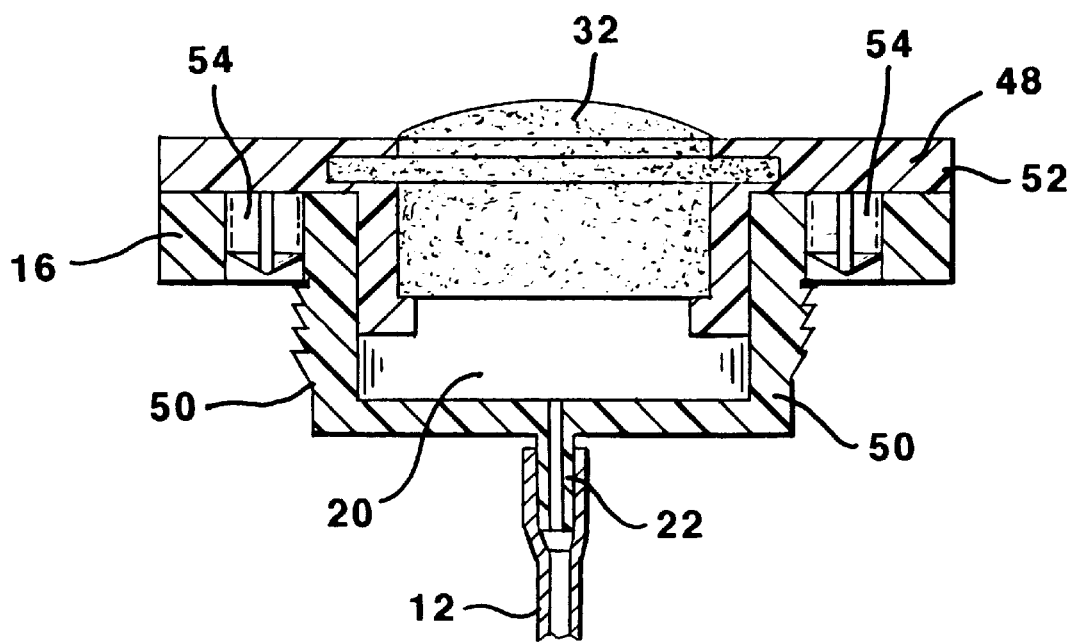
FIG. 4 is an illustration of an exemplary burr hole cap assembly with a catheter for use as an injection port in accordance with the present invention, depicted in a cross-sectional view.

FIGS. 4–7 show a third and fourth embodiment in accordance with the present invention. The key to both of these embodiments is that the septums or filters or both are removable As illustrated in FIG. 4, the invention comprises a central connection tube 22, a burr hole ring 16, a septum mounting member 48, and a septum 32. The central connection tube 22 is attached to the lower portion 50 of burr hole ring 16 to provide fluid communication between a fluid reservoir 20 within burr bole ring 16 and the central lumen of a catheter 12.

Septum mounting member 48 is mountable to burr hole ring 16. Septum 32 is rigidly attached to septum mounting member 48. The septum mounting member 48 can be detachably coupled to burr hole ring 16. Removability allows direct access to the inside of burr hole ring 16. This in turn allows access to the central lumen of catheter 12. Although septum mounting member 48 is detachably coupled to burr hole ring 16, a fluid seal must be formed between the two. This fluid seal is necessary to prevent fluid leakage from fluid reservoir 24 to undesired locations.

In use, septum mounting member 48 is removed from contact with burr hole ring 16. Stylet 14 is placed through burr hole ring 16 into catheter 12. Catheter 12 is placed in a patient's brain 1 as described above. Once catheter 12 is in position, stylet 14 is removed. Then septum mounting member 48 is mounted to burr hole ring 16, thereby sealing burr hole ring 16 and forming a fluid reservoir 24 within burr hole ring 16.

Connecting septum mounting member 48 to burr hole ring 16 may be done by friction fitting or threading the interface between septum mounting member 48 and burr hole ring 16. In addition, septum mounting member 48 may be connected to burr hole ring 16 by configuring the upper flanged section 52 of septum mounting member 48 with split-flanged collets 54. Burr hole ring 16 is configured with a plurality of holes 56 to receive the split-flanged collets 54 protruding from septum mounting member 48. Further, other means for securing the septum mounting member 48 to the burr hole cap 52 are available, e.g. an edge clamping mechanism; screws; etc.

Figure 5:
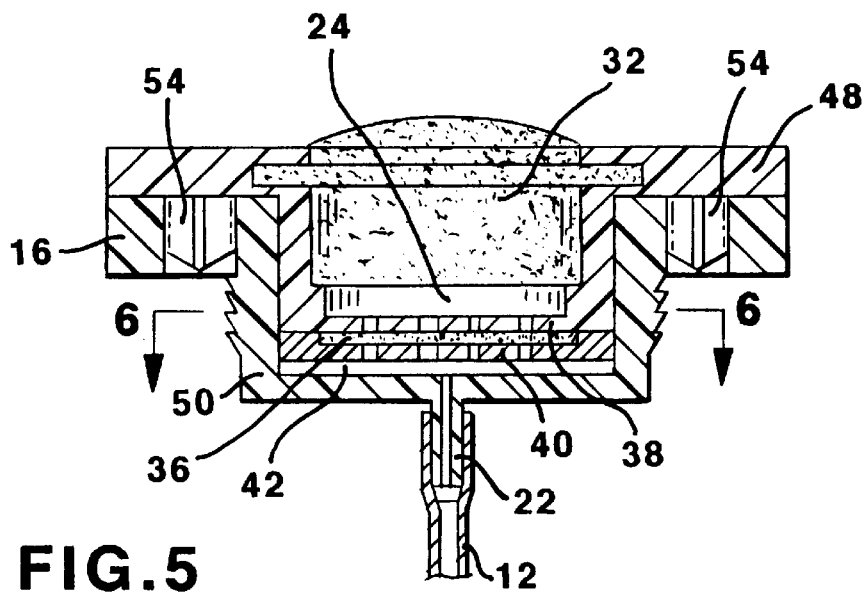
FIG. 5 is an illustration of an exemplary burr hole cap assembly with a catheter for use as an injection port, adapted with an exemplary filter assembly, depicted in a cross-sectional view.
Figure 5A:
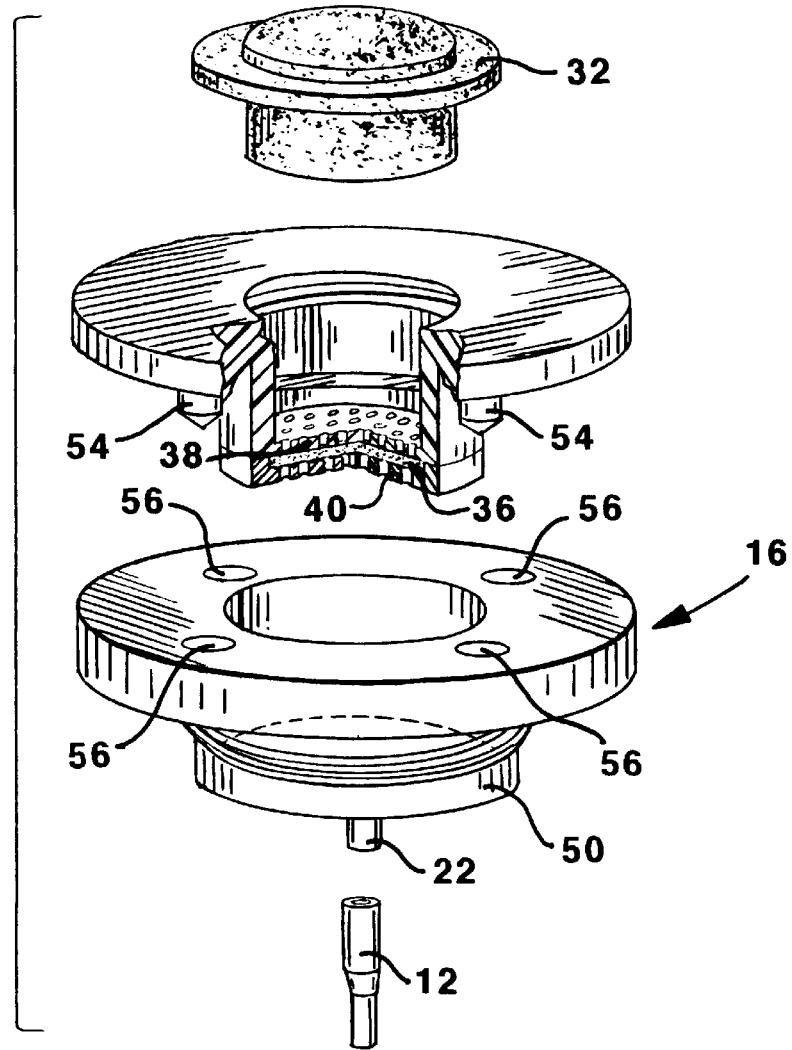
FIG. 5A is an illustration of the assembly shown in FIG. 5, depicted in a three-dimensional exploded view.
Figure 6:
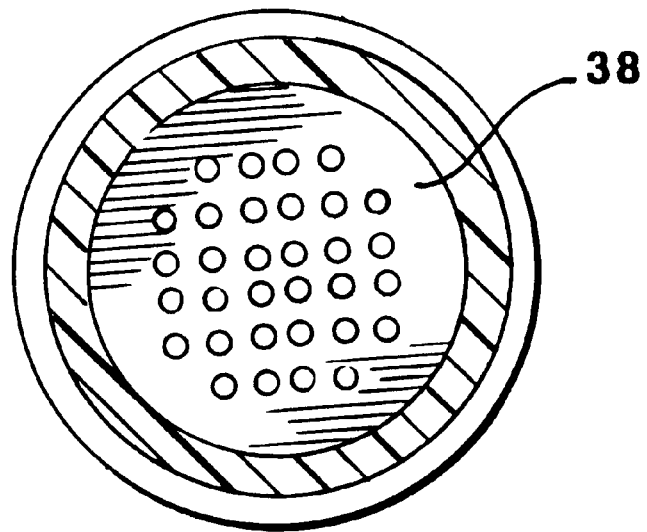
FIG. 6 is an illustration of the assembly shown in FIG. 5, depicted in a cross-sectional view taken along the line 6—6 in FIG. 5.
Figure 7:
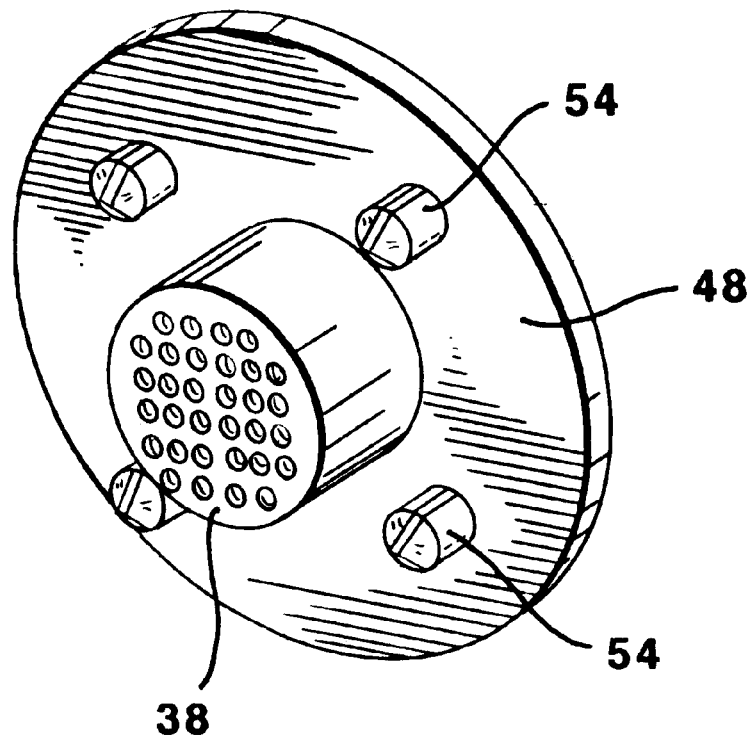
FIG. 7 is an illustration of the filter mounting member of the assembly shown in FIG. 5, depicted in a bottom view.

FIG. 5 shows an alternative embodiment of the invention. In this embodiment, similar elements are referred to with similar reference numbers. In addition, unless stated otherwise, the referenced elements operate as described above.

Septum mounting member 48 is adapted with filter means in the fluid flow path to the catheter 12. The filter means comprises a needle stop 38, filtering layer 36 and a perforated base 40 that function as described above. Preferably, needle stop 38, filtering layer 36 and perforated base 40 are rigidly attached to mounting member 48. The rigid attachment may be either permanent or removable. This connection may be accomplished by ultrasonic welding, adhesives, threads or other mechanical means that will occur to those skilled in the art.

In this embodiment, mounting member 48 is detachable from burr hole ring 16 with the corresponding advantages as described above. In addition, removability permits the exchange of one filter assembly for another when one assembly becomes clogged or otherwise inoperable over time.

As will be appreciated, the devices described herein may be manufactured from a variety of biocompatible materials, including a variety of plastics including, but not limited to, polyurethane, nylon or polysulfone. Although conventional telescoping or bayonet engagement has been depicted between burr hole ring 16 and catheter 12, other configurations could be utilized, including forming catheter 12 integrally with the burr hole ring 16.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the following description of the invention in connection with the accompanying drawings.

What is claimed is:

1. An apparatus for securing a catheter within a burr hole through a patient's skull, comprising:

a housing member configured to be mechanically coupled to said skull proximate said burr hole, said housing member including a generally interior portion, said interior portion being in fluid communication with said catheter;

a septum selectively coupleable to said housing to isolate said interior portion of said housing from a location exterior to said patient's skull, said septum selectively penetrable to provide fluid communication from said location exterior to said skull and said interior portion of said housing member, said septum having a top, wherein said septum and said housing member each include a stylet guiding means comprising an aperture for providing access by a stylet into said catheter.

2. The apparatus of claim 1, wherein said septum is selectively penetrable to provide fluid communication from said location exterior to said skull to a first location within said interior portion of said housing, and wherein said apparatus further comprises a filter assembly in a flow path between said first location within said housing member and said catheter.

3. The apparatus of claim 1, wherein said housing member is configured to mechanically engage said skull adjacent the surfaces of said skull defining said burr hole.

4. The apparatus of claim 1, further comprising retaining members configured to selectively secure said housing member to said skull.

5. The apparatus of claim 4, wherein said retaining members comprise screws.

6. The apparatus of claim 1 wherein said apparatus further comprises a closure member for closing at least said stylet access guidng means in said septum.

7. The apparatus of claim 6 further comprising a stylet tube extending from said top of said septum through said housing member.

8. The apparatus of claim 1 further comprising a stylet.

9. An apparatus for securing a catheter within a burr hole through a patient's skull, comprising:

a housing member configured to mechanically engage the surfaces of said skull defining said burr hole, said housing forming a fluid reservoir, said housing including a connection portion configured to mechanically engage a catheter assembly; and a septum configured to provide selective access to said fluid reservoir from a location exterior to said patient's skull, said septum having a top, wherein said septum and said housing member each include a stylet guiding means comprising an aperture for providing access by a stylet into said catheter.

10. The apparatus of claim 9, wherein a path of fluid communication is formed between said fluid reservoir and said catheter, and wherein said apparatus further comprises a filter member retained within said fluid communication flow path.

11. The apparatus of claim 9, wherein said septum is selectively penetrable to provide fluid communication from said location exterior to said patient's skull to said fluid reservoir.

12. The apparatus of claim 11, wherein said septum is formed of an elastomeric material which is selectively penetrable by a fluid delivery needle.

13. The apparatus of claim 9 wherein said apparatus further comprises a closure member for closing at least said stylet access port in said septum.

14. The apparatus of claim 13 further comprising a stylet tube extending from said top of said septum through said housing member.

15. The apparatus of claim 9 further comprising a stylet.

16. An apparatus for providing fluid access with a patient's brain through a burr hole, comprising:

a burr hole cap assembly engageable with said patient's skull, said burr hole cap assembly comprising a catheter coupled to a fluid exit of a burr hole cap, said catheter extending into said patient's brain, said burr hole ring comprising a fluid chamber and a filter chamber in a fluid path between said fluid chamber and said fluid exit;

a filter element within said filter chamber; and a septum generally isolating said fluid chamber from a location exterior to said patient's skull while allowing penetration by a needle, said septum having a top, wherein said septum and said burr hole cap each include a stylet guiding means comprising an aperture for providing access by a stylet into said catheter.

17. The apparatus of claim 16, wherein said fluid chamber and said filter chamber are separated at least in part by a needle stop surface.

18. The apparatus of claim 16, wherein said catheter is selectively engageable with said burr hole cap.

19. The apparatus of claim 16, wherein said burr hole cap assembly comprises:

a housing member configured to engage the patient's skull; and an inner member which includes said filter chamber and which defines at least a portion of said fluid chamber.

20. The apparatus of claim 16 wherein said apparatus further comprises a closure member for closing at least said stylet access port in said septum.

21. The apparatus of claim 20 further comprising a stylet tube extending from said top of said septum through said burr hole cap assembly.

22. The apparatus of claim 16 further comprising a stylet.

23. A housing member engageable with a patient's skull, said housing member including a first fluid reservoir within said patient's skull, comprising:

a second fluid reservoir at a second location within the patient's body; and a filtering layer within a fluid flow path between said first and second fluid reservoirs, said filtering layer adapted to prevent contaminants within contaminated fluid following the fluid flow path from one reservoir to the other reservoir from passing from the one reservoir to the other reservoir.

24. The apparatus of claim 23, wherein said second fluid reservoir comprises the lumen of an implanted catheter.

25. The apparatus of claim 23, wherein said filtering layer comprises a bioretentive filter material secured within an implantable catheter access port.

26. The apparatus of claim 23, wherein said filtering layer comprises a filter assembly detachably coupled within an implantable catheter access port.

27. An apparatus for providing fluid access with a patient's brain through a burr hole, comprising:

a burr hole cap assembly engageable with said patient's skull, said burr hole cap assembly comprising a catheter coupled to a fluid exit of a burr hole cap, said catheter extending into said patient's brain, said burr hole ring comprising a fluid chamber and a filter chamber in a fluid path between said fluid chamber and said fluid exit;

a filter element within said filter chamber; and a septum generally isolating said fluid chamber from a location exterior to said patient's skull while allowing penetration by a needle, a porous needle stop surface located, at least in part, between said fluid chamber and said filter chamber.

28. The apparatus of claim 27, wherein said catheter is selectively engageable with said burr hole cap.

29. The apparatus of claim 27, wherein said burr hole cap assembly comprises:

a housing member configured to engage the patient's skull; and an inner member which includes said filter chamber and which defines at least a portion of said fluid chamber.

* * * * *